United States Patent [19]

Koenig et al.

[11] 4,314,948

[45] Feb. 9, 1982

[54] PREPARATION OF MIXTURES OF 1-MONOHALOGENATED ISOCYANATES AND 1,2-UNSATURATED ISOCYANATES

[75] Inventors: Karl-Heinz Koenig, Frankenthal; Karl-Heinz Feuerherd; Heinz-Guenter Oeser, both of Ludwigshafen, all of Fed. Rep. of Germany

[73] Assignee: BASF Aktiengesellschaft, Fed. Rep. of Germany

[21] Appl. No.: 175,592

[22] Filed: Aug. 5, 1980

[30] Foreign Application Priority Data

Sep. 13, 1979 [DE] Fed. Rep. of Germany ........ 2937028

[51] Int. Cl.$^3$ ................ C07C 118/00; C07C 119/042; C07C 119/045; C07C 119/048
[52] U.S. Cl. ........................... 260/453 P; 260/453 A; 260/453 AR; 260/453 AL
[58] Field of Search ..... 260/453 P, 453 AL, 453 AR, 260/453 A

[56] References Cited

U.S. PATENT DOCUMENTS

| | | | |
|---|---|---|---|
| 3,437,680 | 4/1969 | Farrissey et al. | 260/453 AR |
| 3,468,923 | 9/1969 | Koenig et al. | 260/453 AL |
| 3,535,360 | 10/1970 | Holtschmidt et al. | 260/453 P |
| 4,231,952 | 11/1980 | Knöfel et al. | 260/453 P |

FOREIGN PATENT DOCUMENTS 1418666 11/1968 Fed. Rep. of Germany.
2639931 3/1978 Fed. Rep. of Germany.

OTHER PUBLICATIONS

J. Org. Chem. 26 (1961), pp. 770–779.
Liebigs Ann. der Chem. 762 (1972), pp. 88–92.
Ber. 102 (1969), pp. 2972–2976.
J. Org. Chem. 32 (1967), pp. 1633–1635.
J. Org. Chem. 28 (1963), pp. 1825–1830.

*Primary Examiner*—Dolph H. Torrence
*Attorney, Agent, or Firm*—Keil & Witherspoon

[57] ABSTRACT

1-Monohalogenated isocyanates, and a process for the preparation of mixtures of 1-monohalogenated isocyanates and 1,2-unsaturated isocyanates by reacting 1-monohalogenated carbamic acid halides or isocyanates with a halogen-free isocyanate or diisocyanate or by reacting 1,2-unsaturated isocyanates with a carbamic acid halide or a bis-carbamic acid halide.

The 1,2-unsaturated isocyanates and 1-monohalogenated isocyanates prepared according to the invention are valuable starting materials for the preparation of pest control agents, dyes, drugs, water-repellent textile finishes, detergents, plastics, bleaches and adhesives.

10 Claims, No Drawings

PREPARATION OF MIXTURES OF 1-MONOHALOGENATED ISOCYANATES AND 1,2-UNSATURATED ISOCYANATES

The present invention relates to novel 1-monohalogenated isocyanates and to a process for the preparation of mixtures of 1-monohalogenated isocyanates and 1,2-unsaturated isocyanates by reacting 1-monohalogenated carbamic acid halides or isocyanates with a halogen-free isocyanate or diisocyanate, or by reacting 1,2-unsaturated isocyanates with a carbamic acid halide or a bis-carbamic acid halide.

It is difficult to synthesize 1-alkenyl isocyanates economically, because these compounds are very reactive; not only are they heat-labile, but they are also sensitive to acids, bases and hydrolysis. The best-known methods of preparation are the Curtius degradation of substituted acrylic acid azides (J. Org. Chem., 26 (1961), 770–779), the pyrolysis of trisvinyl isocyanurates under reduced pressure (German Published Application DAS No. 1,932,811) and the thermal cleavage of N-tert.-alkyl-N-(1-alkenyl)-carbamic acid chlorides (German Published Application DAS No. 1,922,412).

Liebigs Annalen der Chemie, 762 (1972), 88–92, and Ber., 102 (1969), 2,972–2,976, disclose the reaction of the ketimine of diphenyl ketone with phosgene to give a mixture of N-chlorocarbonyl-aralkyl-ketimines and α-chloroaralkyl isocyanates. Polyhalogenated 1-haloalkyl isocyanates and 1-phenyl-1-chloroethyl isocyanate may be obtained by halogenating either unsubstituted or already halogen-substituted alkyl isocyanates and carbamic acid halides (U.S. Pat. No. 3,437,680 and German Laid-Open Application DOS No. 1,418,666).

1-Fluoropropyl isocyanate is obtained, alongside other reaction products, by low temperature fluorination of propyl isocyanate (J. Org. Chem., 32 (1967), 1,633–1,635).

J. Org. Chem., 28 (1963), 1,825–1,830 discloses that chloromethyl isocyanate is obtained by reacting hydroxymethyl isocyanate with thionyl chloride. 1,2,2,2-Tetrachloroethyl isocyanate may be prepared by a similar method.

German Laid-Open Application DOS No. 2,639,931 discloses the reaction of carbamic acid chlorides with organic monoisocyanates or polyisocyanates which boil above the boiling point of the monoisocyanate which is to be prepared, and isolating the resulting monoisocyanate by distillation or by sweeping out with a stream of inert gas. According to the claim and description of the said DOS, the carbon chain bonded to the nitrogen of the carbamic acid chloride remains unchanged; hydrogen chloride is merely eliminated from the acid chloride group. The DOS teaches the same to be true when chlorine-substituted aliphatic radicals are present. In the description, only 2chloroethylcarbamic acid chloride is mentioned as a compound containing a chlorinated radical.

The Examples solely refer to the carbamic acid chloride corresponding to methyl isocyanate and a diisocyanate as the other reactant. 1-Halogenated carbamic acid chlorides are not described. The higher-boiling diisocyanate is converted, in the reaction (see page 13), to the corresponding carbamic acid chloride.

We have found that mixtures of 1-monohalogenated isocyanates of the formula

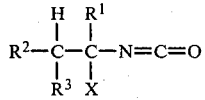

and 1,2-unsaturated isocyanates of the formula

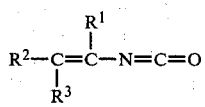

where $R^1$, $R^2$ and $R^3$ may be identical or different and each is hydrogen, alkyl of 1 to 6 carbon atoms or phenyl, or the pair of radicals $R^1$ and $R^2$ together with the two adjacent carbon atoms, or the pair of radicals $R^2$ and $R^3$ together with the adjacent carbon atom, can also form members of a 5-membered or 6-membered alicyclic ring, $R^1$, $R^2$ and $R^3$ in total contain up to 8 carbon atoms, and X is chlorine or bromine, are obtained in an advantageous manner when (a1) 1-monohalogenated carbamic acid halides of the formula

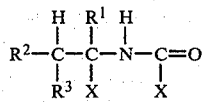

where $R^1$, $R^2$, $R^3$ and X have the above meanings, are reacted with a halogen-free isocyanate of the formula

where $R^4$ is alkyl, cycloalkyl, aryl, aralkyl or alkylaryl, and/or (a2) with a diisocyanate of the formula

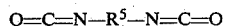

where $R^5$ is alkylene, cycloalkylene, arylene, alkylarylene or arylalkylene, or (b1) 1,2-unsaturated isocyanates Ib are reacted with a 1-halogen-free carbamic acid halide of the formula

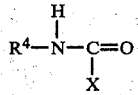

where $R^4$ and X have the above meanings and/or (b2) with a bis-carbamic acid halide of the formula

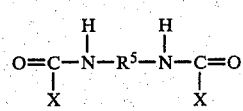

where $R^5$ and X have the above meanings, and/or (b3) with a 1-monohalogenated carbamic acid halide II or (c1) 1-monohalogenated isocyanates Ia are reacted with a halogen-free isocyanate III and/or (c2) with a diisocyanate IV.

Further, we have found the novel 1-monohalogenated isocyanates of the formula

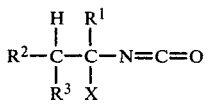

$$\begin{array}{c} \text{H} \quad \text{R}^1 \\ | \quad | \\ \text{R}^2-\text{C}-\text{C}-\text{N}=\text{C}=\text{O} \\ | \quad | \\ \text{R}^3 \quad \text{X} \end{array} \quad \text{Ia}$$

where $R^1$, $R^2$ and $R^3$ may be identical or different and each is hydrogen, alkyl of 1 to 6 carbon atoms or phenyl, or the pair of radicals $R^1$ and $R^2$ together with the two adjacent carbon atoms, or the pair of radicals $R^2$ and $R^3$ together with the adjacent carbon atom, can also form members of a 5-membered or 6-membered alicyclic ring, $R^1$, $R^2$ and $R^3$ in total contain up to 8 carbon atoms, and X is chlorine or bromine, X being bromine if $R^1$ is phenyl and $R^2$ and $R^3$ are each hydrogen.

Where 1-chloroethylcarbamic acid chloride, hexamethylene diisocyanate, vinyl isocyanate, 1-chloroethyl isocyanate and ethyl isocyanate are used, the reaction can be represented by the following equations:

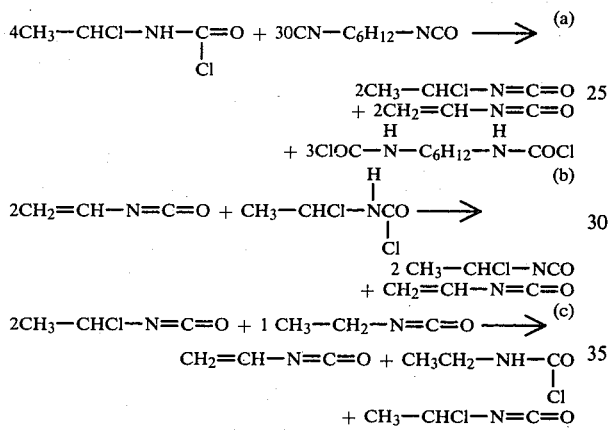

Compared to the prior art, the novel process surprisingly gives 1,2-unsaturated isocyanates and 1-monohalogenated isocyanates more simply and more economically, in good yield and high purity. These advantageous properties of the process according to the invention were not foreseeable since it is known that aliphatic isocyanates react with hydrogen halide even at very low temperatures to give the corresponding carbamic acid halides. These reversibly eliminate hydrogen halide, with slow re-formation of the free isocyanate, on heating. However, this equilibrium cannot be employed, without special measures, for the preparation of the free isocyanates, especially in the case of lower aliphatic isocyanates, since, though the hydrogen halide is liberated on distillation, it seeks to recombine with the isocyanate to form the carbamic acid halide (Houben-Weyl, Methoden der Organischen Chemie, Volume 8, pages 121, 124 and 131). Hence, similar secondary reactions of the starting materials, and corresponding mixtures containing high proportions of the starting materials and their by-products would have been expected. Nor was it to be expected that using the process according to the invention it would prove possible also to eliminate hydrogen halide which originates not from the carbamic acid halide group, but from the atoms of the carbon skeleton, the elimination being accompanied by the formation of an olefinic double bond. The process according to the invention is all the more surprising since 1-alkenyl isocyanates are known to be exceptionally sensitive to hydrogen halide; even at room temperature they form resinous polymeric substances in the presence of hydrogen halide (Recueil, 94 (1975), 102), whilst even at very low temperatures they undergo a spontaneous addition reaction with hydrogen halide (German Laid-Open Application DOS No. 2,732,284). In view of the carbamic acid chloride/isocyanate equilibrium (Houben-Weyl, Methoden der Organischen Chemie, Volume 8, page 121) it would have been expected that the 1-alkenyl isocyanate formed would react with hydrogen halide from as yet unconverted 1-haloalkylcarbamic acid halide, to give polymeric compounds. It is also surprising that using the novel process it is possible to prepare, and isolate by distillation, not only 1-alkenyl isocyanates but also the novel 1-haloalkyl isocyanates.

Furthermore, it is necessary to bear in mind the halogen rearrangement in 1-haloalkyl isocyanates, which results in the following equilibrium (Angew. Chem., 74 (1962), 848):

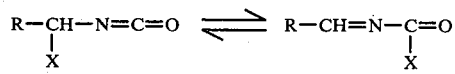

1-Haloalkyl isocyanates are therefore frequently present in the reactive halocarbonylimine form.

It is surprising, in the light of German Laid-Open Application DOS No. 2,639,931, that in case (a), (b1), and (b3) mixtures of 1-halogenated isocyanates and 1,2-unsaturated isocyanates are formed in good yield. It was not to be expected that hydrogen halide would also be eliminated from the 1,2-position.

It was not foreseeable that the isocyanate Ib would undergo addition reaction with hydrogen halide in the 1,2-position, but would not undergo such an addition reaction solely at the isocyanate group without at the same time also undergoing the reaction in the 1,2-position. Surprisingly-in view of this prior publication-the reaction accordingly takes place in the absence of unsaturated carbamic acid halides.

The process of preparation results in mixtures of end products Ia and Ib, the composition of the mixtures depending, in particular, on the chosen starting materials and their ratios, on the choice of processes (a) to (c), on the temperature, and on whether the residual starting materials are removed from the reaction mixture. It is possible to react the starting materials II and III (reaction a 1) or the starting materials II and IV (a 2) or the compounds Ib and V (b 1) or the compounds Ib and VI (b 2) or the compounds Ib and II (b 3) or the compounds Ia and III (c 1) or the compounds Ia and IV (c 2) with one another, in each case in stoichiometric amounts or using an excess of either component; advantageously the excess used is from 15 to 25 moles of compound III per mole of compound II in the case of process (a 1), from 3 to 14 moles of compound IV per mole of compound II in the case of process (a 2), from 0.5 to 1 mole of compound V per mole of compound Ib in the case of process (b 1), from 0.25 to 0.5 mole of compound VI per mole of compound Ib in the case of process (b 2), from 0.5 to 1 mole of compound II per mole of compound Ib in the case of process (b 3), from 7 to 13 moles of compound III per mole of compound Ia in the case of process (c 1) and from 1 to 8 moles of compound IV per mole of compound Ia in the case of process (c 2). In general, reaction (a 1) according to the invention gives mixtures of 0.05 to 0.2 mole of end product Ia per mole of end product Ib, more particularly from 0.05 to 0.1 mole of end product Ia per mole of end product Ib when using the above advantageous amounts of starting materials, reaction (a 2) gives mixtures of from 0.2 to 0.7 mole of end product Ia per mole of end product Ib, more especially from 0.3 to 0.6 mole of end product Ia per mole of end product Ib when using the above advantageous amounts of starting materials, reaction (b 1) gives mixtures of from 0.1 to 1 mole of end product Ia per mole of end product Ib, more especially from 0.1 to 0.5 mole of end product Ia per mole of end product Ib when using the above advantageous amounts of starting materials, reaction (b 2) gives mixtures of from 0.1 to 1 mole of end product Ia per mole of end product Ib, more especially from 0.1 to 0.5 mole of end product Ia per mole of end product Ib when using the above advantageous amounts of starting materials, reaction (b 3) gives mixtures of from 2 to 20 moles of end product Ia per mole of end product Ib, more especially from 7 to 20 moles of end product Ia per mole of end product Ib when using the above advantageous amounts of starting materials, reaction (c1) gives mixtures of from 0.1 to 0.5 mole of end product Ia per mole of end product Ib, more especially from 0.1 to 0.2 mole of end product Ia per mole of end product Ib when using the above advantageous amounts of starting materials, and using the mixed reaction in process c 2 gives mixtures of from 0.1 to 0.4 mole of end product Ia per mole of end product Ib, more especially from 0.1 to 0.2 mole of end product Ia per mole of end product Ib when using the above advantageous amounts of starting materials. The higher the concentration of compounds III in (a1), IV in (a2), V in (b1), VI in (b2), II in (b3), III in (c1) and IV in (c2), compared to the other starting material of the particular case, the greater becomes the proportion of end product Ib in the mixture in the case of process (a1) and correspondingly of Ib in the mixture in process (a2), Ia in the mixture in process (b 1), Ia in the mixture in process (b2), Ia in the mixture in process (b3), Ib in the mixture in process (c1) and Ib in the mixture in process (c2). By carrying out appropriate experiments it is thus easily possible to establish, for each process, the conditions which give the desired ratio of end products Ia and Ib or give substantially only one component in the mixture of end products. In the case of process (b3) substantially only end product Ia is obtained whilst in the case of processes (a1) and (a2) substantially only end product Ib is obtained.

Preferred starting materials II, III, IV, V and VI and accordingly preferred end products Ia and Ib are those where $R^1$, $R^2$ and $R^3$ are identical or different and have the above meanings, alkyl being particularly advantageously of 1 or 2 carbon atoms, $R^4$ is alkyl of 1 to 12, especially 1 to 6, carbon atoms, cyclohexyl, aralkyl or alkylaryl of 7 to 12 carbon atoms or phenyl, $R^5$ is alkylene of 1 to 12 carbon atoms, especially 1 to 6 carbon atoms, cyclohexylene, aralkylene or alkylarylene of 7 to 12 carbon atoms, or phenylene, and X is bromine or, in particular, chlorine. Cycloalkyl $R^4$ and cycloalkylene $R^5$ can advantageously be a monocyclic or bicyclic radical which may or may not be substituted by alkyl of 1 to 3 carbon atoms; in the case of a bicyclic radical, the two cycloalkyl nuclei may be fused or may be directly linked or via a methylene group, and in the case of the starting materials IV the two isocyanato groups may be located as follows: (1) both on a single cycloalkyl nucleus (monocyclic radicals) or (2) both on one of the two cycloalkyl nuclei or (3) one group on one of the two cycloalkyl radicals and the other isocyanato group on the other of the two cycloalkyl radicals or (4) one or both isocyanato groups linked to one or both cycloalkyl nuclei (one isocyanato group linked to one cycloalkyl nucleus, or two isocyanato groups linked to one cycloalkyl nucleus or to two different cycloalkyl nuclei) via alkylene of 1 to 3 carbon atoms. The starting materials II are prepared in a simple manner, for example as described in German Laid-Open Application DOS No. 2,741,980. The end products Ia isolated from the mixture after reaction, for example by distillation, may be re-used as starting materials in process (c1) or (c2), and accordingly the end products Ib may be re-used as starting materials in process (b1), (b2) or (b3), in a reaction according to the invention, so as to achieve a high proportion of one or other end product. If desired, it is also possible to react the starting material II with a mixture of starting materials III and IV, the isocyanate Ib with a mixture of starting materials V and VI, or II and VI, or II and V or II, V and VI, and the isocyanate Ia with a mixture of starting materials III and IV.

Examples of suitable starting materials II are 1-chloroethylcarbamic acid chloride, 1-bromoethylcarbamic acid bromide, 1-chloropropylcarbamic acid chloride, 1-bromopropylcarbamic acid bromide, 1-chloro-1-methylethylcarbamic acid chloride, 1-bromo-1-methylethylcarbamic acid bromide, 2-chlorobut-2-yl-carbamic acid chloride, 2-bromobut-2-yl-carbamic acid bromide, 1-chloro-2-methylpropylcarbamic acid chloride, 1-bromo-2-methylpropylcarbamic acid bromide, 2-chloro-3-methylbut-2-yl-carbamic acid chloride, 2-bromo-3-methylbut-2-yl-carbamic acid bromide, 2-phenyl-1-chloroethylcarbamic acid chloride, 1-chlorocyclohex-1-yl-carbamic acid chloride and 1-chloro-1-cyclohexylethyl-carbamic acid chloride.

Examples of suitable starting materials III and V are ethyl isocyanate, propyl isocyanate, isopropyl isocyanate, butyl isocyanate, isobutyl isocyanate, sec.-butyl isocyanate, tert.-butyl isocyanate, pentyl isocyanate, 3-methyl-butyl isocyanate, hexyl isocyanate, 2-ethylhexyl isocyanate, cyclohexyl isocyanate, phenyl isocyanate, benzyl isocyanate, 3-methylphenyl isocyanate and α-naphthyl isocyanate, and carbamic acid chlorides and carbamic acid bromides corresponding to the above monoisocyanates III.

Examples of suitable starting materials IV and VI are hexamethylene diisocyanate, toluylene diisocyanate, bis-(3-methyl-4-isocyanato-cyclohexyl)-methane, 1,1,4,4-tetramethylbutane 1,4-diisocyanate, 1,1,6,6-tetramethylhexane 1,6-diisocyanate and 3-isocyanatomethyl-3,5,5-trimethylcyclohexyl isocyanate, and biscarbamic acid chlorides and bis-carbamic acid bromides corresponding to the above diisocyanates IV.

Examples of suitable isocyanates Ia or Ib for processes (b1) to (b3), and (c1) and (c2), are the isocyanates corresponding to the carbamic acid halides II listed above as being suitable.

In selecting the starting materials II to VI it is advantageous to take note of the boiling point of the 1,2-unsaturated isocyanate Ib to be expected from a reaction according to the invention. The boiling point of this isocyanate should be at least slightly, but preferably substantially, below, advantageously from 10° to 100° C. below, the boiling points of the starting materials II to VI. Equally, the boiling point of the 1-haloalkyl isocyanate should be substantially lower, advantageously from 10° to 50° C., lower, than that of the starting materials II to VI. Alternatively, on distilling off a mixture of two or three components, for example a mixture of the isocyanates Ia, Ib and III, the content of end product Ia may be almost completely converted to the desired isocyanate Ib by renewed distillation of the mixture in order to obtain the starting material III. A preferred method of carrying out the process according to the invention is to remove the desired mixture, or one of the end products, preferably the end product Ib, immediately and continuously from the equilibrium by means of a stream of inert gas under atmospheric pressure, especially in the case of low-boiling reaction products, or to carry out the reaction under reduced pressure or to combine the use of a stream of inert gas with working under reduced pressure, though the use of a stream of inert gas alone, for example a stream of dry nitrogen or dry air, is preferred.

If, in the case of method (a1) or (a2), a sharp isolation of the isocyanate Ib is not achievable from a single reaction of the 1-halocarbamic acid halid II, the crude end product mixture entrained in the stream of carrier gas can advantageously be reacted afresh with starting material III or IV to give the desired 1,2-unsaturated isocyanate. The reaction residue, which predominantly consists of the carbamic acid chloride corresponding to the starting materials III or IV, can be used to regenerate the isocyanate in a known manner, for example by thermal elimination of hydrogen halide and subsequent distillation of the crude isocyanate, in which case the hydrogen halide liberated can be used separately, for example to prepare aqueous hydrohalic acid, ie. all of the hydrogen halide eliminated can be economically re-used and recycled. In most cases, it is possible to isolate pure 1,2-unsaturated isocyanates Ib, whilst 1-haloisocyanates Ia can, at room temperature, mostly only be obtained in from 70 to 90 percent by weight purity, because these compounds, surprisingly, exist in equilibrium with the corresponding 1-alkenyl isocyanates even at room temperature.

The higher the reaction temperature and the longer the reaction time, the higher is the proportion of end product Ib in the final mixture. The reaction is as a rule carried out at from 0° to 150° C., advantageously from 0° to 50° C. in the case of the preparation of mixtures containing more than 1.5, in particular from above 1.5 to 20 moles, of end product Ia per mole of end product Ib, from 40° to 70° C. in the case of the preparation of mixtures containing from 0.5 to 1.5, especially from 0.9 to 1.1, moles of end product Ia per mole of Ib, and from 70° to 120° C. in the case of the preparation of mixtures containing less than 0.5, in particular from 0.05 to less than 0.5, mole of end product Ia per mole of end product Ib; it is carried out under atmospheric or superatmospheric pressure, continuously or batchwise. Advantageously, the reaction is started at from 0° to 30° C., the temperature is raised slowly and the reaction is completed at the advantageous reaction temperatures mentioned above. The reaction time is in general from 0.1 to 5 hours, advantageously from 2 to 4 hours in the case of the preparation of mixtures containing more than 1.5, in particular from above 1.5 to 20, moles of end product Ia per mole of end product Ib, from 0.5 to 3 hours in the case of the preparation of mixtures containing from 0.5 to 1.5, especially from 0.9 to 1.1, moles of end product Ia per mole of end product Ib, and from 1.5 to 3 hours in the case of the preparation of mixtures containing less than 0.5, especially from 0.05 to less than 0.5, mole of end product Ia per mole of end product Ib. The conversion of the carbamic acid halide group of the 1-halocarbamic acid halide II to the isocyanate group starts even at low temperatures of around +10° C., so that using a sufficiently strong stream of inert gas the equilibrium content of 1-haloisocyanate Ia can be swept out, whilst at higher temperatures, from 30° C. upward, increased formation of the corresponding 1,2-unsaturated isocyanate is to be expected.

In an advantageous embodiment, substantially only end product Ib is prepared by starting the reaction (a1) or (a2) at from 0° to 50° C., completing it at from above 50° to 150° C., and removing the resulting end product Ib during the reaction. Advantageously, the end product is removed by carrying out a fractional distillation, and/or passing in inert gas, for example nitrogen, through the reaction mixture, whilst the reaction is proceeding.

Preferably, the reaction is carried out in the absence of any added solvent, though solvents which are inert under the reaction conditions can be used. Examples of such solvents are aromatic hydrocarbons, eg. toluene, ethylbenzene, o-, m- and p-xylene, isopropylbenzene and methylnaphthalene; halohydrocarbons, especially chlorohydrocarbons, eg. tetrachloroethylene, 1,1,2,2- and 1,1,1,2-tetrachloroethane, dichloropropane, methylene chloride, dichlorobutane, isopropyl bromide, n-propyl bromide, butyl bromide, chloroform, ethyl iodide, propyl iodide, carbon tetrachloride, 1,1,1- and 1,1,2-trichloroethane and trichloroethylene; aliphatic and cycloaliphatic hydrocarbons, eg. heptane, nonane, gasoline fractions boiling within the range from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane; and mixtures of these. Advantageously, the solvent is used in an amount of from 200 to 10,000 percent by weight, preferably from 300 to 2,000 percent by weight, based on starting material II, or in the case of process (b), based on compound Ia or, in the case of process (c), based on compound Ib.

The reaction can be carried out as follows: a mixture of the starting materials is reacted at the reaction temperature for the periods of time stated above. The end products Ia and Ib are isolated from the reaction mixture during or after the reaction, advantageously by raising the temperature and effecting a fractional distillation. Instead of using the pure 1-halocarbamic acid halides II, it is also possible to use the reaction mixtures resulting from the preparation of these starting materials, for example the crude mixtures which result from the halogenation of alkyl isocyanates or of the corresponding carbamic acid halides.

The 1,2-unsaturated isocyanates Ib and 1-monohalogenated isocyanates Ia prepared according to the invention are valuable starting materials for the preparation of pest control agents, dyes, drugs, water-repellent textile finishes, detergents, plastics, bleaches and adhesives, since they contain an activated double bond or activated α-carbon atom in addition to a reactive isocyanate group. Furthermore, 1-alkenyl isocyanates are important monomers which can be converted in various ways to chain polymers and ladder polymers, eg. irradiation-curing surface-coating resins (Chem. High Polymers (Tokyo) 13 (1956), page 390; J. Polymer Sc. 35 (1959), 215, J. Org. Chem. 26 (1961), 770 and J. of Coatings Techn. 49 (1977), 82). They can be converted to urethanes, for example for use as foams or very flexible high molecular weight coatings, or to ureas. Regarding their use, reference may be made to the publications cited earlier and to Ullmanns Encyklopädie der technischen Chemie, Volume 9, pages 11, 12 and 404, and Volume 17, page 204 (3rd edition).

In the Examples which follow, parts are by weight and bear the same relation to parts by volume as that of the kilogram to the liter.

EXAMPLE 1

A solution of 57 parts of 1-chloroethylcarbamic acid chloride in 100 parts by volume of hexamethylene diisocyanate is introduced slowly in the course of half an hour, at 100° C., under the surface of 572 parts of hexamethylene diisocyanate. At the same time nitrogen is blown through the solution and the exit gas is cooled to −100° C. in a cold trap. After the reaction, the reaction mixture is subjected to fractional distillation. 10.2 parts (36.8% of theory) of vinyl isocyanate of boiling point 38.5° C./1013 mbar and 6.8 parts (16.1% of theory) of 1-chloroethyl isocyanate of boiling point 92° C./1013 mbar are obtained.

EXAMPLE 2

30 parts of 1-chloroethylcarbamic acid chloride are dissolved in 100 parts by volume of 1-chloronaphthalene and a solution of 16 parts of vinyl isocyanate in 20 parts by volume of 1-chloronaphthalene is added to the above mixture in the course of 0.3 hour at 2° C.

12.5 parts (8% of theory) of vinyl isocyanate and 43 parts (92% of theory) of 1-chloroethyl isocyanate (determined by gas chromatography) are obtained.

EXAMPLE 3

48.5 parts of 1-bromoethylcarbamic acid bromide are dissolved in 100 parts by volume of α-chloronaphthalene and a solution of 16 parts of vinyl isocyanate in 20 parts by volume of 1-chloronaphthalene is added to the above mixture in the course of 0.4 hour at 2° C. The mixture is then kept at 24° C. for 2 hours. 3.6 parts (11% of theory) of vinyl isocyanate and 58.5 parts (88% of theory) of 1-bromoethyl isocyanate (determined by gas chromatography) are obtained.

EXAMPLE 4

57 parts of 1-chloroethylcarbamic acid chloride are introduced into 700 parts by volume of isopropyl isocyanate at 22° C., the mixture is heated to 70° C. in the course of 1.5 hours whilst passing a slight stream of nitrogen through it, and the reaction mixture is condensed in a cold trap at −70° C. 12 parts (43% of theory) of vinyl isocyanate of boiling point 38.5° C./1013 mbar, 0.85 part (2% of theory) of chloroethyl isocyanate of boiling point 92° C./1013 mbar and 218 parts of isopropyl isocyanate are obtained.

EXAMPLE 5

57 parts of 1-chloroethylcarbamic acid chloride are dissolved in 520 parts of ethyl isocyanate at 22° C. and dry nitrogen is blown through the solution, a Raschig ring column being used to achieve a preliminary separation of the 3-component mixture (ethyl isocyanate, vinyl isocyanate and 1-chloroethyl isocyanate) in the column. The reaction mixture is subjected to fractional distillation for 3 hours. 14 parts (50.5% of theory) of vinyl isocyanate of boiling point 38.5° C./1013 mbar and 466 parts of ethyl isocyanate of boiling point 60° C./1013 mbar are obtained.

EXAMPLE 6

563 parts of 1-chloroethylcarbamic acid chloride are dissolved in 2,800 parts by volume of hexamethylene diisocyanate. The solution, having a total volume of 3,100 parts, is introduced in 3 portions (500, 1,500 and 1,100 parts by volume), with different residence times (150, 310 and 225 minutes respectively), into a thin film evaporator which is operated under atmospheric pressure, with a stream of nitrogen passing through in counter-current. The jacket temperature is 73°–75° C. and the material passes over at 48° to 54° C. The product is collected in a receiver and two downstream cold traps and the composition of the product is determined by gas chromatography. 145.3 parts (53% of theory) of vinyl isocyanate of boiling point 38.5° C./1013 mbar and 73.8 parts (17.7% of theory) of 1-chloroethyl isocyanate of boiling point 92° C./1013 mbar are obtained.

EXAMPLE 7

A mixture of 57 parts of 1-chloroethylcarbamic acid chloride, 156 parts of ethyl isocyanate and 841 parts of hexamethylene diisocyanate is heated to 90° C. in the course of 3 hours, whilst passing a stream of nitrogen at 22° C. through the mixture. A mixture of 11.8 parts (42.5% of theory) of vinyl isocyanate of boiling point 38.5° C./1013 mbar, 10.1 parts (23.8% of theory) of 1-chloroethyl isocyanate of boiling point 92° C./1013 mbar and 149 parts of ethyl isocyanate is obtained in the distillation receiver.

EXAMPLE 8

21 parts of vinyl isocyanate are added to 33 parts of ethylcarbamic acid chloride (dissolved in 100 parts by volume of 1-chloronaphthalene) at 2° C. The temperature of the mixture is raised slowly and the shift of the equilibrium in the reaction mixture, without passing nitrogen through the latter, is followed by gas chromatography; the results are shown in the Table. Ethylcarbamic acid chloride is almost completely converted even at room temperature and is no longer detectable.

TABLE

| Temperature °C. | Yield in % of theory | | |
|---|---|---|---|
| | Vinyl isocyanate | Ethyl isocyanate | α-Chloroethyl isocyanate |
| 20 | 29 | 48 | 22 |
| 40 | 19 | 47 | 33 |
| 50 | 9.7 | 49.6 | 40.7 |

We claim:
1. A process for the preparation of a mixture of 1-monohalogenated isocyanates of the formula

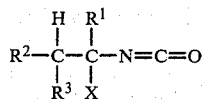

and 1,2-unsaturated isocyanates of the formula

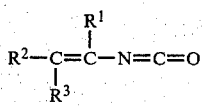

where $R^1$, $R^2$ and $R^3$ may be identical or different and each is hydrogen, alkyl of 1 to 6 carbon atoms or phenyl, or the pair of radicals $R^1$ and $R^2$ together with the two adjacent carbon atoms, or the pair of radicals $R^2$ and $R^3$ together with the adjacent carbon atom, can also form members of a 5-membered or 6-membered alicyclic ring, $R^1$, $R^2$ and $R^3$ in total contain up to 8 carbon atoms, and X is chlorine or bromine, wherein (a1) 1-monohalogenated carbamic acid halides of the formula

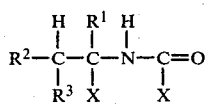
II where $R^1$, $R^2$, $R^3$ and X have the above meanings, are reacted with a halogen-free isocyanate of the formula

III where $R^4$ is alkyl, cycloalkyl, aryl, aralkyl or alkylaryl, and/or
(a2) with a diisocyanate of the formula

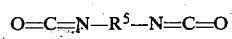
IV where $R^5$ is alkylene, cycloalkylene, arylene, alkylarylene or arylalkylene, or
(b1) 1,2-unsaturated isocyanates Ib are reacted with a 1-halogen-free carbamic acid halide of the formula

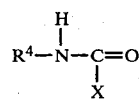
V where $R^4$ and X have the above meanings and/or
(b2) with a bis-carbamic acid halide of the formula

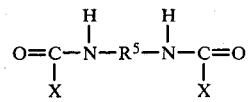
VI where $R^5$ and X have the above meanings, and/or
(b3) with a 1-monohalogenated carbamic acid halide II or
(c1) 1-monohalogenated isocyanates Ia are reacted with a halogen-free isocyanate III and/or
(c2) with a diisocyanate IV.

2. A process as claimed in claim 1, wherein the reaction, in the case of process (a1), is carried out with from 15 to 25 moles of compound III per mole of compound II.

3. A process as claimed in claim 1, wherein the reaction, in the case of process (a2), is carried out with from 3 to 14 moles of compound IV per mole of compound II.

4. A process as claimed in claim 1, wherein the reaction, in the case of process (b1), is carried out with from 0.5 to 1 mole of compound V per mole of compound Ib.

5. A process as claimed in claim 1, wherein the reaction, in the case of process (b2), is carried out with from 0.25 to 0.5 mole of compound VI per mole of compound Ib.

6. A process as claimed in claim 1, wherein the reaction, in the case of process (b3), is carried out with from 0.5 to 1 mole of compound II per mole of compound Ib.

7. A process as claimed in claim 1, wherein the reaction, in the case of process (c1), is carried out with from 7 to 13 moles of compound III per mole of compound Ia.

8. A process as claimed in claim 1, wherein the reaction, in the case of process (c2), is carried out with from 1 to 8 moles of compound IV per mole of compound Ia.

9. A process as claimed in claim 1, wherein the reaction is carried out at from 0° to 150° C.

10. A process as claimed in claim 1, wherein the reaction time is from 0.1 to 5 hours.

* * * * *